US009031194B2

(12) United States Patent
Nishii

(10) Patent No.: US 9,031,194 B2
(45) Date of Patent: May 12, 2015

(54) X-RAY IMAGING APPARATUS, METHOD FOR X-RAY IMAGING APPARATUS AND NON-TRANSITORY COMPUTER-READABLE RECORDING MEDIUM

(75) Inventor: Yuichi Nishii, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 380 days.

(21) Appl. No.: 13/411,766

(22) Filed: Mar. 5, 2012

(65) Prior Publication Data
US 2012/0243664 A1 Sep. 27, 2012

(30) Foreign Application Priority Data

Mar. 23, 2011 (JP) ................................. 2011-064827

(51) Int. Cl.
A61B 6/00 (2006.01)
A61B 6/10 (2006.01)

(52) U.S. Cl.
CPC .................. A61B 6/465 (2013.01); A61B 6/461 (2013.01); A61B 6/46 (2013.01); A61B 6/463 (2013.01); A61B 6/107 (2013.01); A61B 6/487 (2013.01); A61B 6/542 (2013.01)

(58) Field of Classification Search
CPC ........... A61B 6/46; A61B 6/461; A61B 6/465
USPC .......................................... 378/98, 98.2, 165
See application file for complete search history.

(56) References Cited

U.S. PATENT DOCUMENTS 6,879,661 B2 * 4/2005 Tsuchino ....................... 378/116
7,129,499 B2 * 10/2006 Nokita ...................... 250/370.09
7,720,523 B2 * 5/2010 Omernick et al. ............. 600/427
8,053,737 B2 * 11/2011 Ohta et al. ................ 250/370.09
8,074,273 B2 * 12/2011 Oowaki et al. .................. 726/17
8,080,802 B2 * 12/2011 Nishino et al. ........... 250/370.08
8,558,176 B2 * 10/2013 Komori et al. ............. 250/336.1
8,621,346 B2 * 12/2013 Ikeda et al. .................... 715/272
2011/0052016 A1 3/2011 Nishii ............................ 382/128
2012/0128129 A1 5/2012 Nishii .............................. 378/98

FOREIGN PATENT DOCUMENTS

| EP | 1191342 | | 3/2002 | |
|---|---|---|---|---|
| EP | 1 813 191 | | 8/2007 | |
| EP | 1825811 | | 8/2007 | |
| EP | 2248465 | | 11/2010 | |
| GB | 2489559 | A * | 10/2012 | ............... A61B 6/00 |
| JP | 2003-211799 | | 7/2003 | |

(Continued)

OTHER PUBLICATIONS

Search Report and Written Opinion issued on Jan. 20, 2014 (search completed Dec. 18, 2013) in counterpart Dutch patent application NL 2008510, with translation.

(Continued)

Primary Examiner — Allen C. Ho

(74) Attorney, Agent, or Firm — Fitzpatrick, Cella, Harper & Scinto

(57) ABSTRACT

An X-ray imaging apparatus comprises: an obtaining unit configured to obtain an operational state of a connected apparatus; and a display control unit configured to control a transition to a hide display state in accordance with the obtained operational state, wherein the hide display state comprises performing display while hiding at least part of information displayed on a display device.

6 Claims, 5 Drawing Sheets

(56) References Cited

FOREIGN PATENT DOCUMENTS

| | | | |
|---|---|---|---|
| JP | 2003/290196 | 10/2003 | |
| JP | 2003290196 A * | 10/2003 | ............... A61B 6/00 |
| JP | 2006-230648 | 9/2006 | |
| JP | 2006-326187 | 12/2006 | |
| JP | 2010-017221 | 1/2010 | |
| JP | 2010017221 A * | 1/2010 | ............... A61B 5/00 |
| WO | WO 2006/054699 A1 * | 5/2006 | |
| WO | WO 2007/010484 A1 | 1/2007 | |

OTHER PUBLICATIONS

Communication (Office Action) issued Jun. 29, 2012, in counterpart British patent application 1204203.2.

Office Action issued on Mar. 5, 2014 in counterpart PRC patent application 201210080532.1, with translation.

* cited by examiner

X-RAY IMAGING APPARATUS, METHOD FOR X-RAY IMAGING APPARATUS AND NON-TRANSITORY COMPUTER-READABLE RECORDING MEDIUM

BACKGROUND OF THE INVENTION

1. Field of the Invention

The present invention relates to an X-ray imaging apparatus, a method for an X-ray imaging apparatus and a non-transitory computer readable recording medium and, more particularly, to an X-ray imaging apparatus, a method for an X-ray imaging apparatus and a non-transitory computer readable recording medium, which changes the display form of a display device in accordance with the driving status of an X-ray imaging unit.

2. Description of the Related Art

There is a growing need to improve efficiency and speed up examination by digitizing and storing/transmitting medical image information of patients which are generated in a hospital. Under this circumstance, in the field of direct imaging, an X-ray imaging system which outputs digital data using an X-ray detection apparatus such as an FPD (Flat Panel Detector) in place of a conventionally used screen/film system has been increasingly used.

A conventional X-ray imaging system is connected to an X-ray detection apparatus to transmit an image sensing control signal to the X-ray detection apparatus to control its image sensing operation, and obtains X-ray image data sensed based on the image sensing control signal from the X-ray detection apparatus. There has been proposed an X-ray imaging system which displays X-ray image data and performs image processing and management, management of patient information, and management of an image sensing sequence.

In such an X-ray imaging system, a technique has been proposed of erasing display screen or displaying a moving image on the screen by executing information hide display processing when no input operation is performed for a predetermined time or more from an input device such as a mouse, keyboard, trackball, or irradiation switch. Information hide display processing has been originally proposed to prevent burn-in on the display screen. Recently, however, this processing is often used for the purpose of personal information protection. As mentioned in the HIPAA law in the U.S., personal information protection is indispensable to the medical and nursing care fields, and hence information hide display processing is implemented as a method of protecting personal information.

With regard to conventional information hide display processing, Japanese Patent Laid-Open No. 2003-290196 discloses the invention of implementing the end of a screen saver in response to a change in information within a self apparatus.

A conventional X-ray imaging system, however, has the following problems. The conventional X-ray imaging system executes information hide display processing when no input operation is performed for a predetermined time or more from an input device in consideration of personal information protection. Even in a state in which image sensing can be started, this system executes information hide display processing when a predetermined time has elapsed.

In this case, the execution of X-ray irradiation processing may collide with the execution of information hide display processing. Such collision may lead to a situation in which no image is displayed in spite of X-ray irradiation.

Since no image is stored upon implementation of X-ray fluoroscopy, in particular, it is impossible to refer to any image after image sensing operation. This may lead to unwanted radiation exposure on a patient.

In consideration of the above problems, the present invention provides a technique of preventing patients from undergoing unwanted radiation exposure.

SUMMARY OF THE INVENTION

According to one aspect of the present invention, there is provided an X-ray imaging apparatus comprising: an obtaining unit configured to obtain an operational state of a connected apparatus; and a display control unit configured to control a transition to a hide display state in accordance with the obtained operational state, wherein the hide display state comprises performing display while hiding at least part of information displayed on a display device.

According to one aspect of the present invention, there is provided a method for an X-ray imaging apparatus comprising: obtaining an operational state of an apparatus connected to the X-ray imaging apparatus; and controlling a transition to a hide display state in accordance with the obtained operational state, wherein the hide display state comprises performing display while hiding at least part of information displayed on a display device.

Further features of the present invention will be apparent from the following description of exemplary embodiments with reference to the attached drawings.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

(First Embodiment)

Figure 1:
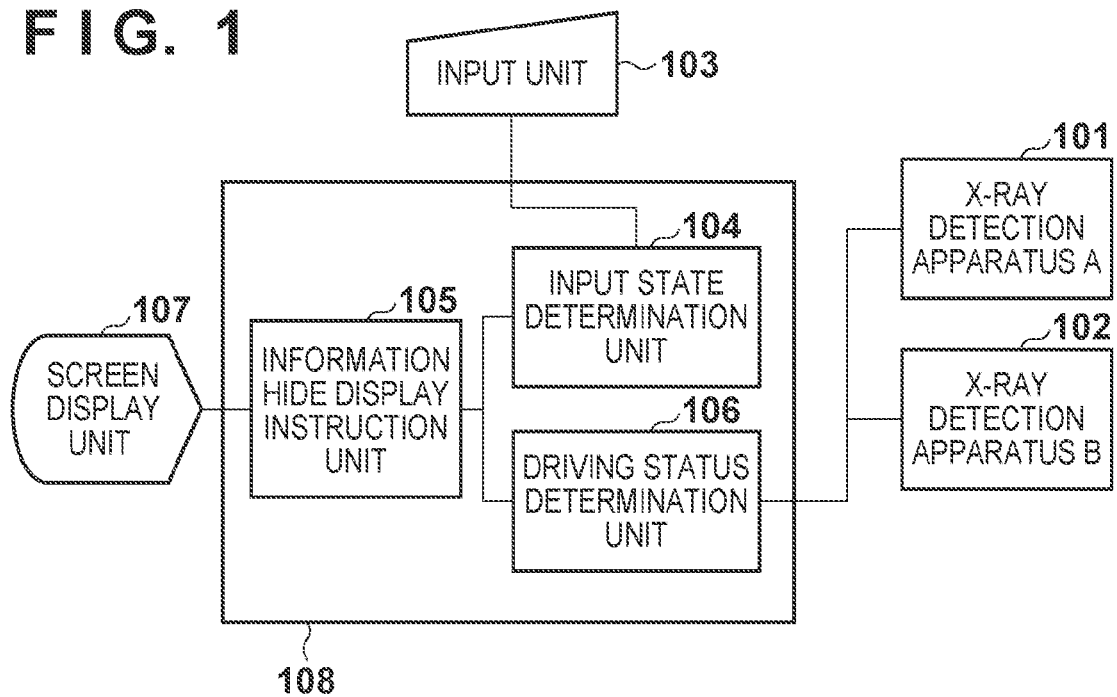
FIG. 1 is a block diagram showing the schematic arrangement of an X-ray imaging system according to the first embodiment.

The first embodiment according to the present invention will be described below with reference to the accompanying drawings. FIG. 1 is a block diagram showing the arrangement of an X-ray imaging apparatus 108 according to this embodiment. The X-ray imaging apparatus 108 includes an input state determination unit 104, an information hide display instruction unit 105, and a driving status determination unit 106. The input state determination unit 104 is connected to an input unit 103. The information hide display instruction unit 105 is connected to a screen display unit 107. The driving status determination unit 106 is connected to an X-ray detection apparatus A (X-ray detection apparatus 101) and an X-ray detection apparatus B (X-ray detection apparatus 102). A CPU (not shown) mounted in the X-ray imaging apparatus 108 controls each processing unit. The CPU reads out a control program stored in a storage unit (not shown), and controls each processing unit by executing the control program.

The X-ray detection apparatus A (X-ray detection apparatus 101) and the X-ray detection apparatus B (X-ray detection apparatus 102) detect irradiated X-rays. The input unit 103 accepts inputs from an outside source such as the user (input acceptance). The input unit 103 is an external input device of the X-ray imaging apparatus 108. However, the X-ray imaging apparatus 108 may incorporate the input unit 103. The input state determination unit 104 determines whether there is an input from the input unit 103 after the lapse of a predetermined time.

Based on information from the input state determination unit 104 and the driving status determination unit 106, the information hide display instruction unit 105 instructs the screen display unit 107 to hide/display part or all of the information output to the screen display unit 107 in consideration of personal information and the purpose of saving power and preventing burn-in.

The driving status determination unit 106 determines a non-driving status when all the connected apparatuses, that is, the X-ray detection apparatus A (X-ray detection apparatus 101) and the X-ray detection apparatus B (X-ray detection apparatus 102), are powered off or in a standby state in which no X-ray imaging is performed. The screen display unit 107 performs display control of various kinds of information. The screen display unit 107 is an external display device of the X-ray imaging apparatus 108. However, the X-ray imaging apparatus 108 may incorporate the screen display unit 107.

Figure 4:
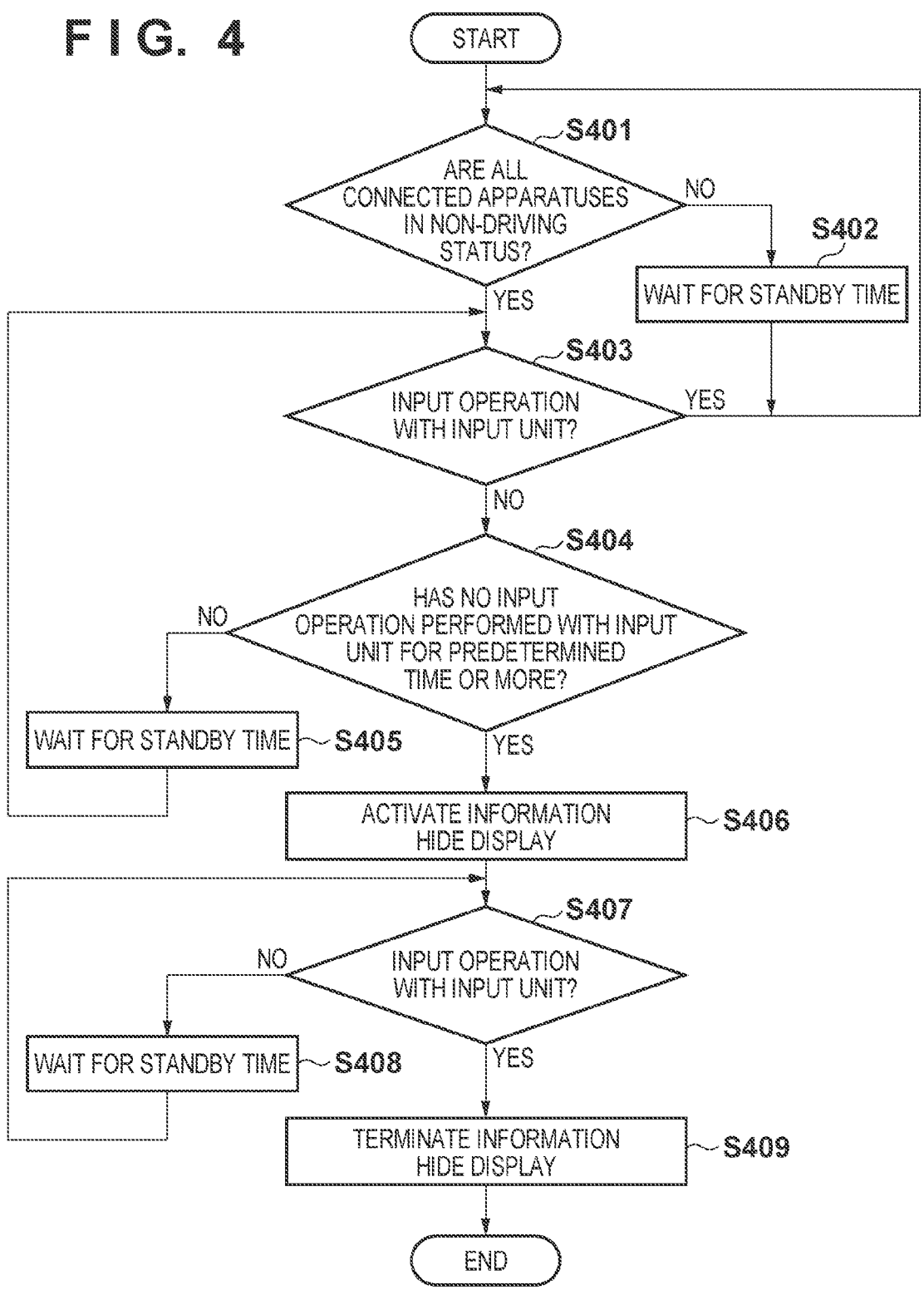
FIG. 4 is a flowchart showing a procedure for information hide processing by an X-ray imaging apparatus.

A procedure for information hide processing by the X-ray imaging apparatus will be described next with reference to the flowchart of FIG. 4.

In step S401, the driving status determination unit 106 determines whether all the connected apparatuses, that is, the X-ray detection apparatus A (X-ray detection apparatus 101) and the X-ray detection apparatus B (X-ray detection apparatus 102), are in the non-driving status in which they are powered off or in the standby state (driving status determination processing). If they are in the non-driving status, the X-ray imaging apparatus 108 can determine that it cannot immediately implement fluoroscopy or image sensing. If the driving status determination unit 106 determines that all the connected apparatuses are in the non-driving status (YES in step S401), the process advances to step S403. If the driving status determination unit 106 determines that at least one of all the connected apparatuses is powered on and is not in the standby state, that is, in an image sensing preparation state (NO in step S401), the process advances to step S402.

After a predetermined standby time (predetermined time) has elapsed in step S402, the process returns to step S401. The input state determination unit 104 determines in step S403 whether input operation has been performed with the input unit 103 (input determination processing). If the input state determination unit 104 determines that input operation has been performed (YES in step S403), the process returns to step S401. If the input state determination unit 104 determines that no input operation has been performed (NO in step S403), the process advances to step S404.

In step S404, the input state determination unit 104 determines whether no input operation has been performed with the input unit 103 for a predetermined time or more. If the input state determination unit 104 determines that no input operation has been performed for the predetermined time or more (YES in step S404), the process advances to step S406. If the input state determination unit 104 determines that input operation has been performed within the predetermined time (NO in step S404), the process advances to step S405.

After the lapse of a predetermined standby time in step S405, the process returns to step S403. In step S406, the information hide display instruction unit 105 implements information hide display processing because the non-driving status continues for the predetermined time. For example, it is possible to hide information by displaying a screen saver. In addition, it is possible to hide only information part or the overall window including the information.

In step S407, the input state determination unit 104 determines whether input operation has been performed with the input unit 103. If the input state determination unit 104 determines that input operation has been performed (YES in step S407), the process advances to step S409. If the input state determination unit 104 determines that no input operation has been performed (NO in step S407), the process advances to step S408.

After the lapse of the predetermined standby time in step S408, the process returns to step S407. In step S409, the information hide display instruction unit 105 terminates the information hide display processing. The series of processing then ends.

Figure 5:
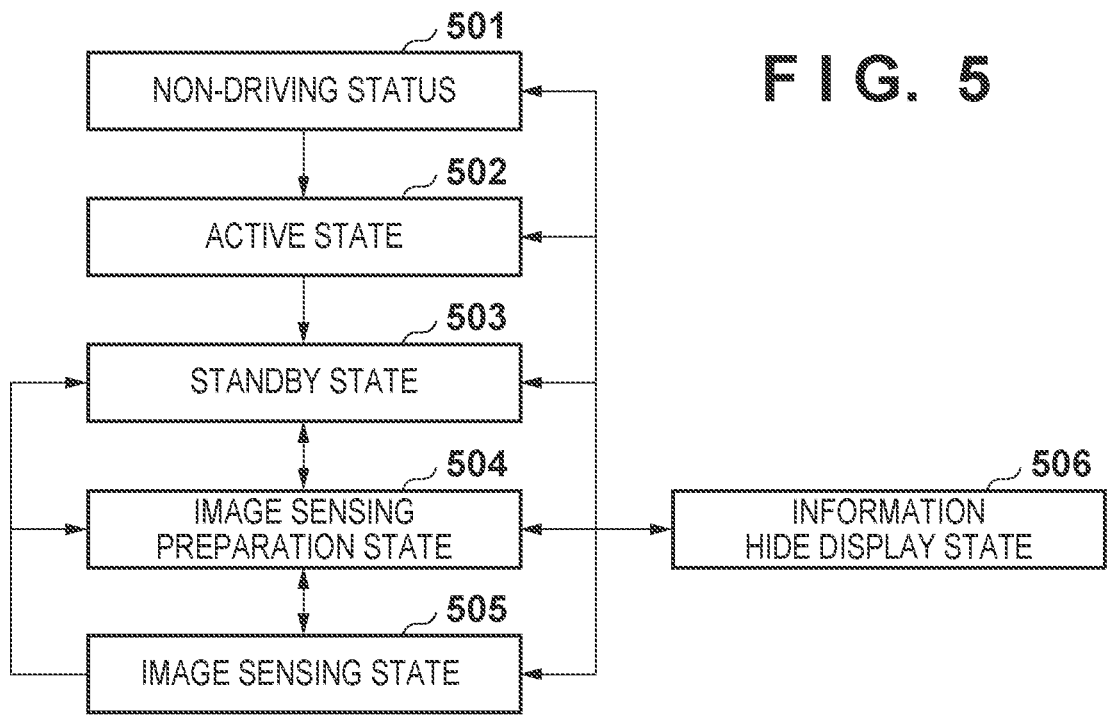
FIG. 5 is a view showing a conventional state in which transitions occur to an information hide display state.
Figure 6:
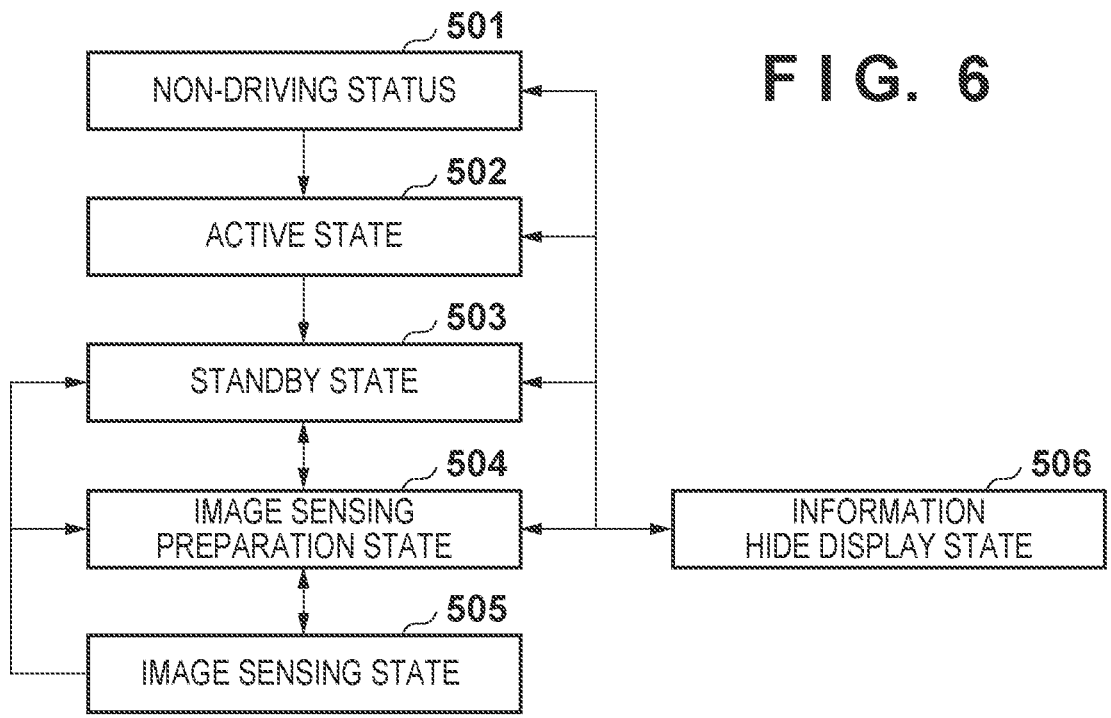
FIG. 6 is a view showing a conventional state in which transitions occur to an information hide display state.

FIGS. 5 and 6 show the possibilities of transition between states which an X-ray imaging apparatus 108 can conventionally take. In this case, each unidirectional arrow indicates that a transition can be made from a given state to another state, and each bidirectional arrow indicates that a transition can be made mutually between a given state and another state. The states which the X-ray imaging apparatus 108 can conventionally take include non-driving state 501, an active state 502, a standby state 503, an image sensing preparation state 504, an image sensing state 505, and an information hide display state 506. Referring to FIG. 5, the information hide display state 506 allows transitions between itself and all the remaining states. Referring to FIG. 6, the information hide display state 506 allows transitions between itself and all the remaining states except for the image sensing state 505. That is, in either case, a transition can be made from the image sensing preparation state 504 to the information hide display state 506, that is, it might appear that a transition to the image sensing state 505 may collide with a transition to the information hide display state 506.

Figure 7:
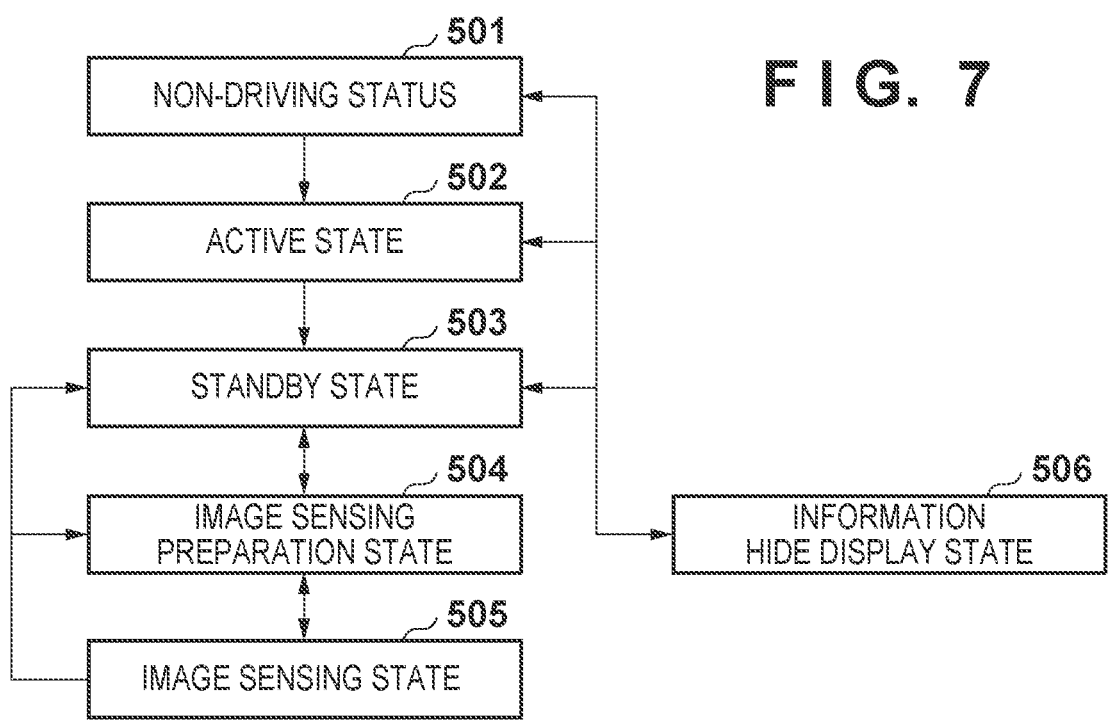
FIG. 7 a view showing a state according to the present invention in which transitions occur to an information hide display state.

According to this embodiment, however, as shown in FIG. 7, the information hide display state 506 allows transitions only between itself and the non-driving state 501, the active state 502, and the standby state 503. This can prevent the occurrence of collision. This makes it possible to prevent patients from undergoing unwanted radiation exposure.

(Second Embodiment)

Figure 2:
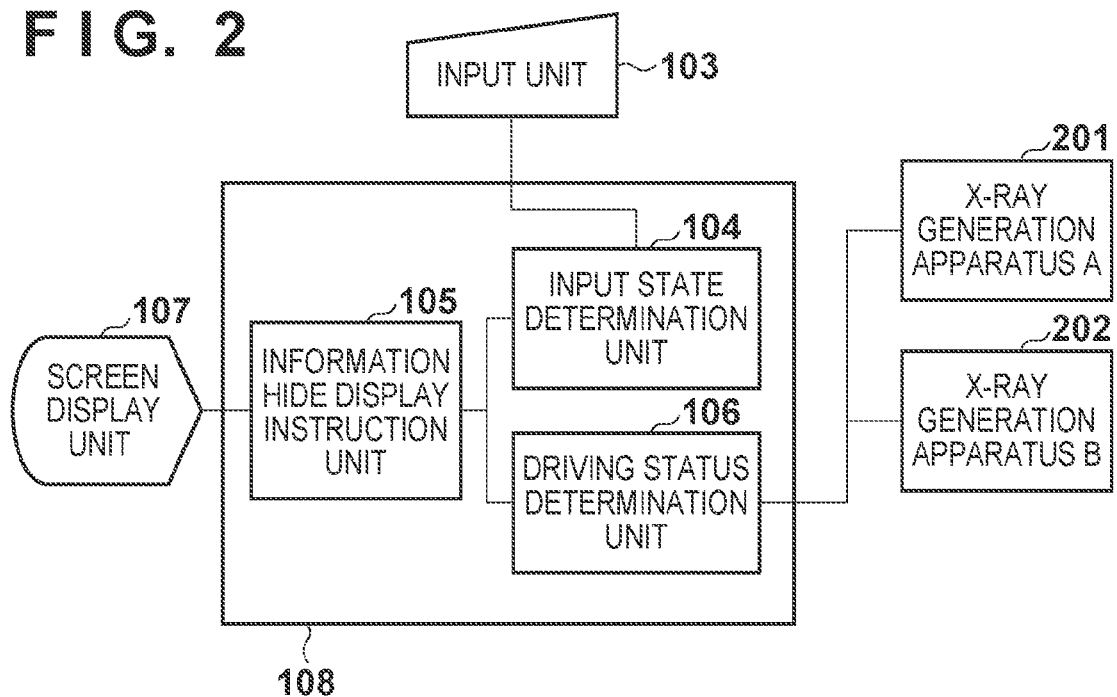
FIG. 2 is a block diagram showing the schematic arrangement of an X-ray imaging system according to the second embodiment.

The second embodiment according to the present invention will be described below with reference to the accompanying drawings. FIG. 2 is a block diagram showing the arrangement of an X-ray imaging apparatus 108 according to this embodiment. The same reference numerals as in the first embodiment denote the same constituent elements in the second embodiment, and a description of them will be omitted. The second embodiment differs from the first embodiment in that a driving status determination unit 106 of the X-ray imaging apparatus 108 is connected to an X-ray generation apparatus A (X-ray generation apparatus 201) and an X-ray generation apparatus B (X-ray generation apparatus 202). All the connected apparatuses according to this embodiment are the X-ray generation apparatus A (X-ray generation apparatus 201) and the X-ray generation apparatus B (X-ray generation apparatus 202). This embodiment differs from the first embodiment in the connected apparatuses, and performs processing similar to the processing procedure described with reference to the flowchart of FIG. 4.

(Third Embodiment)

Figure 3:
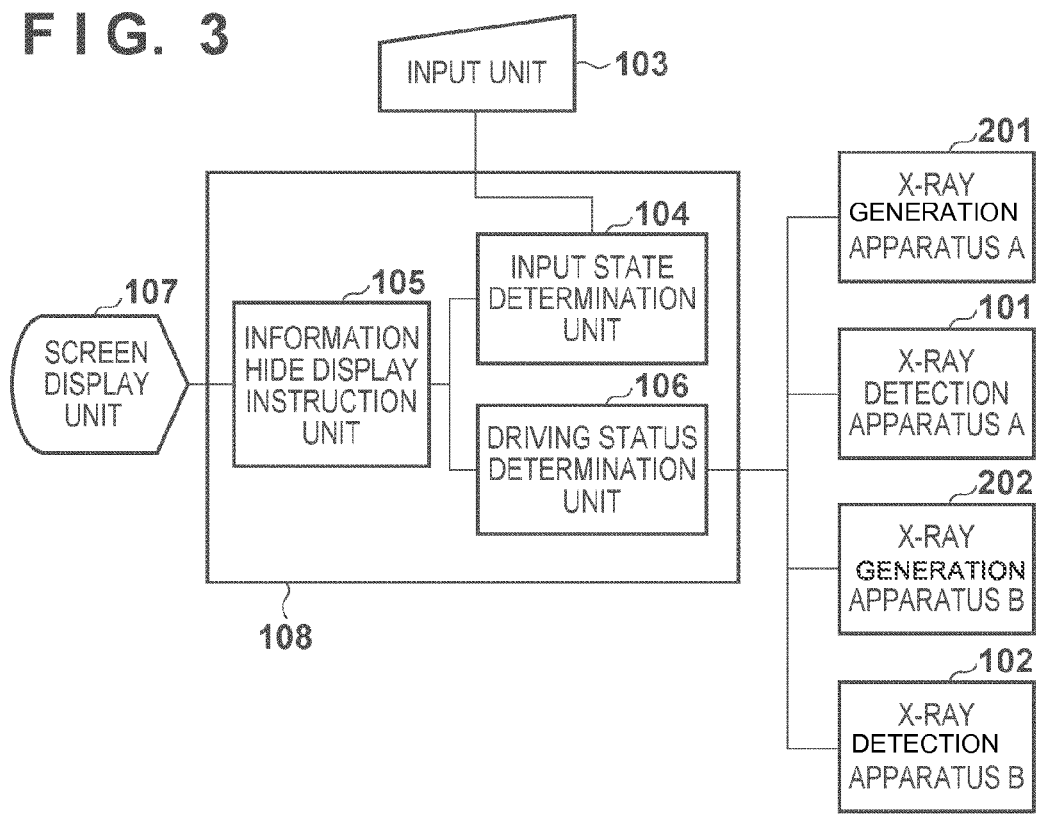
FIG. 3 is a block diagram showing the schematic arrangement of an X-ray imaging system according to the third embodiment.

The third embodiment according to the present invention will be described below with reference to the accompanying drawings. FIG. 3 is a block diagram showing the arrangement of an X-ray imaging apparatus 108 according to this embodiment. The same reference numerals as in the first embodiment denote the same constituent elements in the third embodiment, and a description of them will be omitted. The third embodiment differs from the first embodiment in that a driving status determination unit 106 of the X-ray imaging apparatus 108 is connected to an X-ray detection apparatus A (X-ray detection apparatus 101), an X-ray detection apparatus B (X-ray detection apparatus 102), an X-ray generation apparatus A (X-ray generation apparatus 201), and an X-ray generation apparatus B (X-ray generation apparatus 202). All the connected apparatuses according to this embodiment are the X-ray detection apparatus A (X-ray detection apparatus 101), the X-ray detection apparatus B (X-ray detection apparatus 102), the X-ray generation apparatus A (X-ray generation apparatus 201), and the X-ray generation apparatus B (X-ray generation apparatus 202). This embodiment differs from the first embodiment only in the connected apparatuses, and performs processing similar to the processing procedure described with reference to the flowchart of FIG. 4.

The present invention can prevent patients from undergoing unwanted radiation exposure.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-064827 filed on Mar. 23, 2011, which is hereby incorporated by reference herein in its entirety.

What is claimed is:

1. An X-ray imaging apparatus comprising:
an obtaining unit configured to obtain an operational state of an X-ray detection apparatus, which detects X-rays, and to obtain an input determining state of an input acceptance apparatus that is connected to the X-ray imaging apparatus, wherein the input determining state is for determining whether there is any input from a user at the input acceptance apparatus for a predetermined time;
a driving status determination unit configured to determine that the X-ray detection apparatus is in a non-driving status when the X-ray detection apparatus is powered off or in a standby state in which no X-ray imaging is performed;
a display control unit configured to control a transition to an information hide display state of a display device based on both the obtained operational state of the X-ray detection apparatus and the obtained input determining state of the input acceptance apparatus, wherein said display control unit is configured such that if (a) said driving status determination unit determines that the X-ray detection apparatus is in the non-driving state and (b) said obtaining unit determines that no input from the user has been received at the input acceptance apparatus for the predetermined time, then said display control unit transitions to the information hide display state.

2. The X-ray imaging apparatus according to claim 1, wherein said display control unit is configured to inhibit the information hide display state from being activated when the X-ray detection apparatus is in one of an image sensing state and an image sensing preparation state.

3. The X-ray imaging apparatus according to claim 1, wherein if said driving status determination unit determines that the X-ray detection apparatus is not in the non-driving status, said driving status determination unit determines again whether the X-ray detection apparatus is in the non-driving status, after a predetermined time elapses.

4. The X-ray imaging apparatus according to claim 1, wherein said obtaining unit is further configured to determine whether the input from the user is received by the input acceptance apparatus after said display control unit transitions to the information hide display state, and
wherein said display control unit is configured to terminate the information hide display state when said obtaining unit determines that the input from the user is received by the input acceptance apparatus.

5. A method of operating an X-ray imaging apparatus comprising:
obtaining an operational state of an X-ray detection apparatus, which detects X-rays, and obtaining an input determining state of an input acceptance apparatus connected to the X-ray imaging apparatus, wherein the input determining state is for determining whether there is any input from a user at the input acceptance apparatus for a predetermined time;
determining that the X-ray detection apparatus is in a non-driving status when the X-ray detection apparatus is powered off or in a standby state in which no X-ray imaging is performed;
controlling a transition to an information hide display state of a display device based on both the obtained operational state of the X-ray detection apparatus and the obtained input determining state of the input acceptance apparatus,
wherein said controlling step is performed such that if it is determined in said determining step (a) that the X-ray detection apparatus is in the non-driving state and (b) that no input from the user has been received at the input acceptance apparatus for the predetermined time, then transition to the information hide display state is performed.

6. A non-transitory computer-readable recording medium storing a program which when run on a computer in an X-ray imaging apparatus causes the computer in the X-ray imaging apparatus to:
obtain an operational state of an X-ray detection apparatus, which detects X-rays, and obtain an input determining state of an input acceptance apparatus connected to the X-ray imaging apparatus, wherein the input determining state is for determining whether there is any input from a user at the input acceptance apparatus for a predetermined time;

determine that the X-ray detection apparatus is in a non-driving status when the X-ray detection apparatus is powered off or in a standby state in which no X-ray imaging is performed; and control a transition to an information hide display state of a display device based on both the obtained operational state of the X-ray detection apparatus and the obtained input determining state of the input acceptance apparatus, wherein said control is performed such that if it is determined (a) that the X-ray detection apparatus is in the non-driving state and (b) that no input from the user has been received at the input acceptance apparatus for the predetermined time, then transition to the information hide display state is performed.

* * * * *